United States Patent
Varney

(10) Patent No.: US 11,000,654 B2
(45) Date of Patent: May 11, 2021

(54) RESPIRATORY THERAPY APPARATUS AND METHODS

(71) Applicant: SMITHS MEDICAL INTERNATIONAL LIMITED, Ashford (GB)

(72) Inventor: Mark Sinclair Varney, Bedfordshire (GB)

(73) Assignee: SMITHS MEDICAL INTERNATIONAL LIMITED, Ashford (GB)

( * ) Notice: Subject to any disclaimer, the term of this patent is extended or adjusted under 35 U.S.C. 154(b) by 1189 days.

(21) Appl. No.: 14/898,159

(22) PCT Filed: May 14, 2014

(86) PCT No.: PCT/GB2014/000184
§ 371 (c)(1),
(2) Date: Dec. 14, 2015

(87) PCT Pub. No.: WO2014/202924
PCT Pub. Date: Dec. 24, 2014

(65) Prior Publication Data
US 2016/0136367 A1  May 19, 2016

(30) Foreign Application Priority Data
Jun. 18, 2013 (GB) ..................... 1310826

(51) Int. Cl.
*A61M 16/00* (2006.01)
*A63B 21/00* (2006.01)
(Continued)

(52) U.S. Cl.
CPC ........ *A61M 16/0006* (2014.02); *A61M 16/20* (2013.01); *A63B 21/00192* (2013.01);
(Continued)

(58) Field of Classification Search
CPC ................................................. A61M 16/0006
See application file for complete search history.

(56) References Cited

U.S. PATENT DOCUMENTS

| 3,640,133 A | * | 2/1972 | Adams ..................... F15C 1/08 73/861.19 |
| 5,018,517 A | | 5/1991 | Liardet |

(Continued)

FOREIGN PATENT DOCUMENTS

| EP | 1338296 A1 | 8/2003 |
| EP | 1 900 387 | 3/2008 |

(Continued)

OTHER PUBLICATIONS

PCT International Search Report and Written Opinion of the ISA/EP, PCT/GB2014/000184, dated Jul. 21, 2014.
(Continued)

*Primary Examiner* — Samchuan C Yao
*Assistant Examiner* — Cana A Gallegos
(74) *Attorney, Agent, or Firm* — Louis Woo

(57) ABSTRACT

A vibratory PEP respiratory therapy device (100) includes a valve element (11) on a rocker arm (12) that opens and closes an opening (10) during exhalation through the apparatus. An accelerometer (20) including a piezoelectric beam (22) supported at one end (23) is mounted on the outside of the housing (2) of the device to respond to vibration transmitted though the housing caused by oscillating movement of the rocker arm (12). The output of the accelerometer (20) is supplied to a circuit (28), (29) that determines when the device (100) is used and the duration and quality of use of the device.

11 Claims, 3 Drawing Sheets

(51) Int. Cl.
*A61M 16/20* (2006.01)
*A63B 23/18* (2006.01)
*A61B 5/00* (2006.01)

(52) U.S. Cl.
CPC ............ *A63B 23/18* (2013.01); *A61B 5/4833* (2013.01); *A61M 16/205* (2014.02); *A61M 16/208* (2013.01); *A61M 2205/0294* (2013.01); *A61M 2205/332* (2013.01); *A61M 2205/3331* (2013.01); *A61M 2205/3375* (2013.01); *A61M 2205/3569* (2013.01); *A61M 2205/3592* (2013.01); *A61M 2205/502* (2013.01); *A61M 2205/52* (2013.01); *A63B 2220/40* (2013.01); *A63B 2220/58* (2013.01)

(56) References Cited

U.S. PATENT DOCUMENTS

| | | | |
|---|---|---|---|
| 5,451,190 A | 9/1995 | Liardet | |
| 5,544,647 A * | 8/1996 | Jewett | A61M 15/009 128/200.23 |
| 6,076,392 A * | 6/2000 | Drzewiecki | A61M 16/0051 73/23.2 |
| 6,328,033 B1 * | 12/2001 | Avrahami | A61M 15/0085 128/200.25 |
| 6,581,596 B1 * | 6/2003 | Truitt | A61M 16/00 128/204.18 |
| 6,581,598 B1 | 6/2003 | Foran et al. | |
| 6,776,159 B2 | 8/2004 | Pelerossi et al. | |
| 7,059,324 B2 | 6/2006 | Pelerossi et al. | |
| 7,699,054 B2 | 4/2010 | Pelerossi et al. | |
| 8,807,131 B1 * | 8/2014 | Tunnell | A61M 16/0051 128/200.23 |
| 2003/0127092 A1 * | 7/2003 | Pelerossi | A61M 16/08 128/200.24 |
| 2003/0216671 A1 | 11/2003 | Saruwarati | |
| 2003/0234017 A1 | 12/2003 | Pelerossi et al. | |
| 2004/0187871 A1 | 9/2004 | Kimmel et al. | |
| 2005/0124375 A1 | 6/2005 | Nowosielski | |
| 2006/0090753 A1 | 5/2006 | Pelerossi et al. | |
| 2006/0212273 A1 | 9/2006 | Krausman et al. | |
| 2007/0023039 A1 | 2/2007 | Ishizaki et al. | |
| 2007/0089740 A1 | 4/2007 | Baumert et al. | |
| 2011/0100112 A1 * | 5/2011 | Du | E21B 47/10 73/152.32 |
| 2011/0125044 A1 | 5/2011 | Rhee et al. | |
| 2012/0012106 A1 * | 1/2012 | Bari | A61M 15/009 128/200.23 |
| 2012/0247235 A1 * | 10/2012 | Adamo | A61B 5/08 73/865.4 |
| 2014/0352702 A1 * | 12/2014 | Abramson | A61N 2/004 128/848 |
| 2015/0122261 A1 * | 5/2015 | Pettitt | A63B 23/18 128/205.24 |

FOREIGN PATENT DOCUMENTS

| | | |
|---|---|---|
| EP | 1 908 489 | 4/2008 |
| WO | 9904687 A2 | 2/1999 |
| WO | 2009013670 A2 | 1/2009 |
| WO | 2012026963 A2 | 3/2012 |
| WO | 20120038903 A2 | 3/2012 |
| WO | WO 2012/085756 | 6/2012 |
| WO | WO 2012/095764 | 7/2012 |
| WO | 2012104513 A2 | 8/2012 |
| WO | WO 2012/104513 | 8/2012 |

OTHER PUBLICATIONS

EP14727016 Opposition by opposer dated Jan. 10, 2020.
Article "Physuotherapy without problem or addicted to Physiotherapy?", Mucoviscidose, publication date Feb. 2007, Seite 1, Von 2.
Hippokratia, Oct.-Dec. 2008; 12(4):211-220.
Article "MiniSense 100NM Vibration Sensor", Measurement Specialities(TM), published Jan. 8, 2011.
Holmes, Martin et al., "Automatic Identification and Accurate Temporal Detection of Inhalations in Asthma Inhaler Recordings" IEEE Engineering in Medicine and Biology Society, Aug. 2012.
Kuan "A Frame Work for Automatic Heart and Lung Sound Analysis Using a Mobile Telemedicine Platform", Dissertation, MIT. Dec. 16, 2010.
Buozin "Kine Sans Accroc ou Accro a La Kine", Mucoviscidose, vol. 112, Feb. 2007.
Papadopoulou "Current Devices of Respiratory Physiotherapy", Hippokratia vol. 12, No. 4, 2008.
Wang et al. "Mobile Phone Based Health Technology", Recent Patents on Biomedical Engineering, vol. 2, 15-21, 2009.
EP3010396 Notice of Opposition.

* cited by examiner

RESPIRATORY THERAPY APPARATUS AND METHODS

This invention relates to respiratory therapy apparatus of the kind including a device having a structure and a movable member mounted with the structure that is caused to oscillate by the action of breathing through the device.

The invention is also concerned with methods of evaluating patient use of respiratory therapy apparatus.

Positive expiratory pressure (PEP) apparatus, that is, apparatus that presents a resistance to expiration through the device, are now widely used to help treat patients suffering from a range of respiratory impairments, such as chronic obstructive pulmonary disease, bronchitis, cystic fibrosis and atelectasis. More recently, such apparatus that provide an alternating resistance to flow have been found to be particularly effective. One example of such apparatus is sold under the trade mark Acapella (a registered trade mark of Smiths Medical) by Smiths Medical and is described in U.S. Pat. Nos. 6,581,598, 6,776,159, 7,059,324 and 7,699,054. Other vibratory respiratory therapy apparatus is available, such as "Quake" manufactured by Thayer, "AeroPEP" manufactured by Monaghan, "TheraPEP" manufactured by Smiths Medical and "IPV Percussionator" manufactured by Percussionaire Corp. Alternative apparatus such as "Cough-Assist" manufactured by Philips is also available. Respiratory therapy apparatus can instead provide an alternating resistance to flow during inhalation.

To be effective these apparatus must be used regularly at prescribed intervals. In the case of chronic diseases, the patient needs to use the apparatus daily for the rest of his life in order to maintain continuous relief.

Although these apparatus can be very effective, users often neglect to use the apparatus regularly at the prescribed frequency. It is very difficult to maintain a record of use of the apparatus, especially when the patient is using it at home. The clinician often does not know whether deterioration in a patient's condition is because he has failed to use the apparatus as prescribed or whether other factors are the cause.

It is an object of the present invention to provide alternative respiratory therapy apparatus.

According to one aspect of the present invention there is provided a respiratory therapy apparatus of the above-specified kind, characterised in that the apparatus includes a sensor mounted with the structure and responsive to vibration transmitted through the structure caused by the oscillating movement of the movable member to provide a signal indicative of use of the device.

The structure preferably includes an outer housing of the device. The sensor is preferably mounted on the outside of the outer housing. The sensor may include an accelerometer. The sensor may include a beam including a piezoelectric element, the beam being supported at one end such that vibration transmitted through the structure causes the beam to flex and produces a change of output from the piezoelectric element. The beam preferably supports a mass towards an opposite end. The device may include a store for storing the output of the sensor. The apparatus may be arranged to provide an output representation indicative of one or more of the following: when the apparatus is used, the duration of use and the quality of use of the apparatus. The apparatus may include a valve element on a rocker arm that opens and closes an opening during exhalation through the apparatus. The device may be a vibratory PEP therapy device, the device being arranged to produce an oscillating resistance to expiration through the device.

According to another aspect of the present invention there is provide a method of evaluating use of a respiratory therapy device including a structure and a movable member mounted on the structure that is caused to oscillate by the action of breathing through the device, characterised in that the method includes the step of monitoring vibration transmitted through the structure of the device.

The method preferably includes the step of storing an indication of periods of sensed vibration. The method may include the step of determining frequencies of vibration.

According to a further aspect of the present invention there is provided apparatus for use in a method according to the above other aspect of the present invention.

Apparatus including a vibratory PEP device and its method of use according to the present invention will now be described, by way of example, with reference to the accompanying drawings, in which:

FIG. 1 is an exploded view of the apparatus;
FIG. 2 is a perspective view of the interior of the sensor;
FIG. 3 illustrates an alternative form of sensor;
FIG. 4A illustrates the output from a single expiration;
FIG. 4B illustrates the output over a treatment cycle of multiple breaths; and
FIG. 4C illustrates use of the apparatus over a week.

With reference first to FIG. 1, the respiratory therapy device 100 comprises a rocker assembly 1 contained within an outer housing 2 provided by an upper part 3 and a lower part 4 of substantially semi-cylindrical shape. The device is completed by an adjustable dial 5 of circular section. The outer housing 2 contains an air flow tube 6 with a breathing inlet 7 at one end and an inspiratory inlet 8 at the opposite end including a one-way valve (not shown) that allows air to flow into the air flow tube but prevents air flowing out through the inspiratory inlet. The air flow tube 6 has an outlet opening 10 with a non-linear profile that is opened and closed by a conical valve element 11 mounted on a rocker arm 12 pivoted midway along its length about a transverse axis. The air flow tube 6 and housing 2 provide a structure with which the rocker arm 12 is mounted. At its far end, remote from the breathing inlet 7, the rocker arm 12 carries an iron pin 13 that interacts with the magnetic field produced by a permanent magnet (not visible) mounted on an adjustable support frame 14. The magnet arrangement is such that, when the patient is not breathing through the device, the far end of the rocker arm 12 is held down such that its valve element 11 is also held down in sealing engagement with the outlet opening 10. A cam follower projection 15 at one end of the support frame 14 locates in a cam slot 16 in the dial 5 such that, by rotating the dial, the support frame 14, with its magnet, can be moved up or down to alter the strength of the magnetic field interacting with the iron pin 13. The dial 5 enables the frequency of operation and the resistance to flow of air through the device to be adjusted for maximum therapeutic benefit to the user.

When the patient inhales through the breathing inlet 7 air is drawn through the inspiratory inlet 8 and along the air flow tube 6 to the breathing inlet. When the patient exhales, the one-way valve in the inspiratory inlet 8 closes, preventing any air flowing out along this path. Instead, the expiratory pressure is applied to the underside of the valve element 11 on the rocker arm 12 causing it to be lifted up out of the opening 10 against the magnetic attraction, thereby allowing air to flow out to atmosphere. The opening 10 has a non-linear profile, which causes the effective discharge area to increase as the far end of the rocker arm 12 lifts, thereby allowing the arm to fall back down and close the opening. As long as the user keeps applying sufficient expiratory pressure, the rocker arm 12 will rise and fall repeatedly as the opening 10 is opened and closed, causing a vibratory, alternating or oscillating interruption to expiratory breath flow through the device. Further information about the construction and operation of the device can be found in U.S. Pat. No. 6,581,598, the contents of which are hereby incorporated into the present application.

As so far described, the device is conventional.

The apparatus of the present invention includes the device 100 described above and a sensor 20 attached to the structure of the device. In particular, the sensor 20 is attached to the external surface of the housing 2. Although it would be possible to mount the sensor 20 internally within the housing 2, mounting the sensor externally avoids the need to provide electrical access within the device. The sensor 20 is responsive to vibration transmitted through the structure of the device caused by parts of the rocker arm 12 contacting other parts of the device as it oscillates up and down in see-saw fashion. The sensor 20 could be of any conventional kind responsive to vibration, such as an accelerometer. Preferably, however, the sensor 20 includes a piezoelectric element 21 of the kind shown in FIG. 2. The piezoelectric element 21 is a model MiniSense 100NM or MiniSense 100 available from Measurement Specialities, although other piezoelectric sensors could be used. It includes a thin, bendable rectangular beam 22 that is itself of a piezoelectric material or includes a piezoelectric material bonded to a supporting substrate. The beam 22 is supported at one end 23 in cantilever fashion by two pillars 24, which also act as electrodes to provide electrical connection to the element 21, and hold the beam spaced above and parallel to a circuit board 25. The opposite, free end 26 of the beam 22 supports a small mass 27 so that any acceleration in the vertical plane causes the free end of the beam to flex up or down. This flexing of the piezoelectric element 21 causes a charge or voltage to be produced across the output electrodes 24. Vibration transmitted through the structure provided by the air flow tube 6 and the housing 2 causes the piezoelectric element 21 to vibrate at a frequency and with an amplitude dependent on the frequency and magnitude (forcefulness) of oscillation of the rocker arm 12.

The sensor element 21 has a good linearity and dynamic range. The mass 27 may be modified to vary the frequency response and sensitivity. The element 21 may be used to detect either continuous or impulsive vibration or impacts. For excitation frequencies below its resonant frequency, the piezoelectric element 21 produces a linear output governed by the "baseline" sensitivity. The sensitivity at resonance is significantly higher. Impacts containing high frequency components will excite the resonance frequency. The ability of the sensor element 21 to detect low frequency motion is strongly influenced by the external electrical circuit.

The output of the piezoelectric element 21 is supplied to a circuit 29 on the board 25, which is preferably an LDTC MiniSense 100 Analog PCB. The circuit 29 includes a low-power operational amplifier, comparator, DC/DC converter, store and passive components used in signal conditioning and has an adjustable gain. The sensor 20 may itself include processing means or this may be provided externally in a unit 28. In particular, the processing is arranged to convert the output from the piezoelectric element 21 into usable parameters by suitable statistical treatment, such as time-domain or frequency-domain analysis. Conventional signal processing using fast fourier transformation, correlation analysis, finite impulse filters and the like may be used. The sensor 20 also includes a memory for recording the output and may also include a display for providing information to the patient, such as average frequency of vibration, day and time of the therapy sessions, duration of the therapy sessions and an indication of the quality of the exhalation breaths, representing the average pressure or flow as derived from the amplitude of the sensed vibration. The board also has an output socket 120, such as for a USB connector or may have a wireless output, such as using the Bluetooth radio frequency protocol.

Instead of being mounted on a circuit board, the piezoelectric element 21' could be encapsulated in a protective capsule 30 as shown in FIG. 3. The capsule 30 includes little or no processing circuitry but has a connector 31 by which connection can be made to a remote circuit at which the processing and storage can be carried out.

The typical output from the piezoelectric element 21 during a single exhalation is shown in FIG. 4A where the output rises along an approximate square wave with a superimposed alternating signal as the oscillation of the rocker arm 12 becomes more forceful during the exhalation. When the user has exhausted his exhalation breath the rocker arm 12 reverts to a stationary state with the outlet opening 10 closed. When this happens the output of the piezoelectric element 21 rapidly falls.

Figure 1:
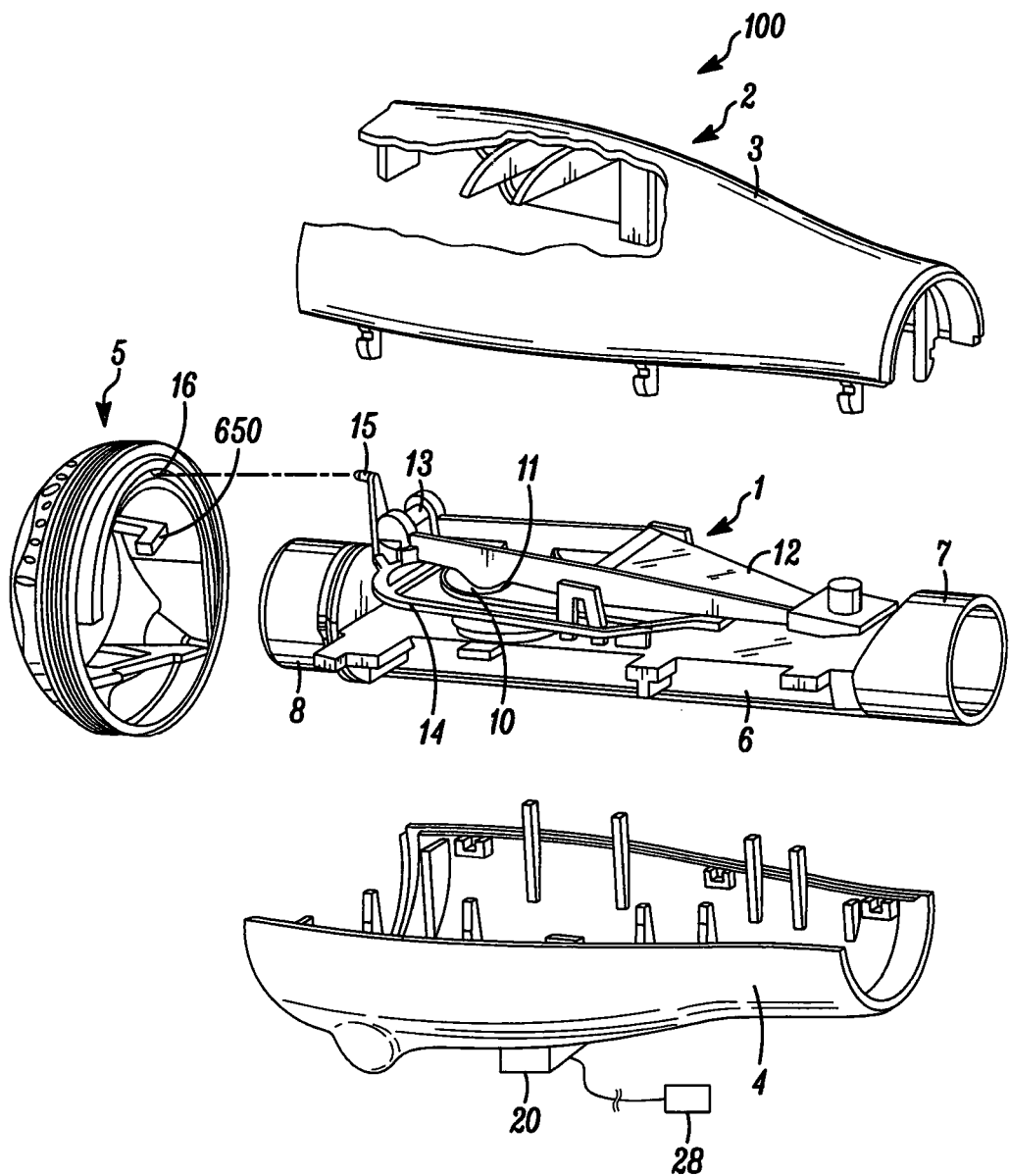
Figure 2:
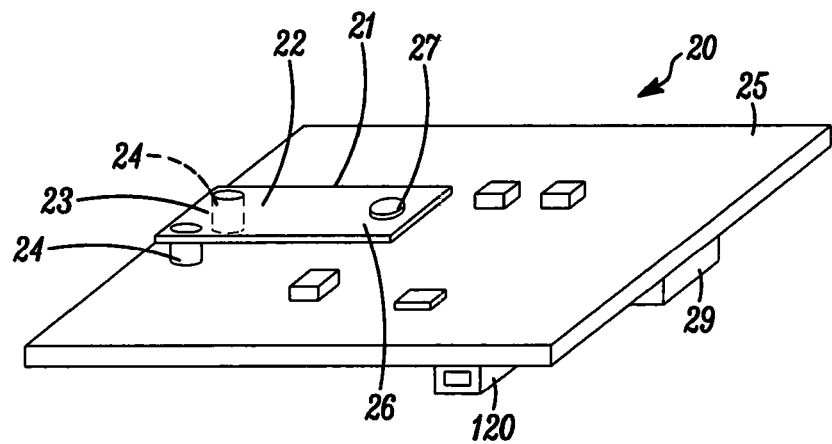
Figure 3:
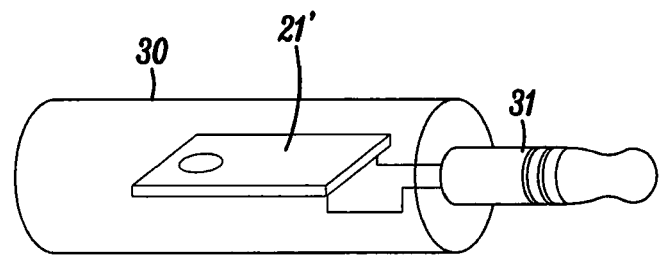
Figure 4A:
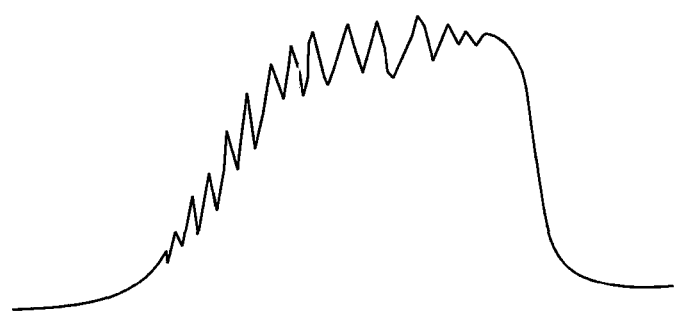
FIG. 4B shows a succession of breaths during a single therapy session.
FIG. 4C shows seven traces, one for each day of the week, with marks indicating when therapy sessions have taken place.
Figure 4B:
Figure 4C:
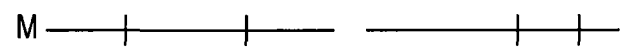
Figure 4C:
Figure 4C:
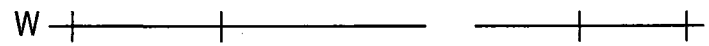
Figure 4C:
Figure 4C:
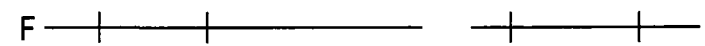
Figure 4C:
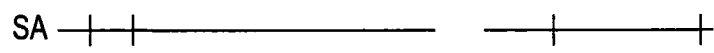
Figure 4C:

It will be appreciated that there are many different ways in which information obtained from the sensor can be represented so that it is provided to the user and clinician in the most useful manner.

Apparatus of the present invention can be used with any conventional respiratory therapy apparatus that produces a vibration. The therapy apparatus may be combined with other treatments such as nebulisation or the administration of aerosol medication.

The present invention enables existing, conventional therapy apparatus that is known and trusted by the user and clinician to be readily modified to provide useful data about use of the apparatus. In this way, the user can be made more aware of how well he is complying with the prescribed therapy programme and can modify his use of the apparatus accordingly to achieve maximum benefit. The clinician is also able to check patient compliance so that he can identify whether any deterioration in a patient's condition is due to lack of compliance or if alternative treatment is needed.

The invention claimed is:

1. A respiratory therapy apparatus including a vibratory therapy device having a housing and a movable member mounted in the housing that is caused to oscillate by the action of breathing through the housing so as to provide an oscillating resistance to breathing through the housing, characterized in that the housing includes an inlet through which a patient breathes and an outlet through which gas flows, the movable member mounted between the inlet and the outlet, an accelerometer mounted on the housing and responsive to vibration transmitted through the housing caused by the oscillating movement of the movable member to provide a signal indicative of the oscillatory movement of the movable member within the housing caused by breathing through the apparatus and indicative of the use of the vibratory therapy device.

2. The respiratory therapy apparatus according to claim 1, characterized in that the accelerometer includes a beam including a piezoelectric element, and that the beam is supported at one end such that vibration transmitted through the housing causes the beam to flex and produces a change of output from the piezoelectric element.

3. The respiratory therapy apparatus according to claim 2, characterized in that the beam supports a mass towards an opposite end.

4. The respiratory therapy apparatus according to claim 1, characterized in that the apparatus includes a store for storing the output of the sensor.

5. The respiratory therapy apparatus according to claim 1, characterized in that the apparatus is arranged to provide an output representation indicative of one or more of the following: when the apparatus is used, the duration of use and the quality of use of the apparatus.

6. The respiratory therapy apparatus according to claim 1, characterized in that the apparatus includes a valve element on a rocker arm in the housing that opens and closes an opening in the housing during exhalation through the housing.

7. The respiratory therapy apparatus according to claim 1, characterized in that the device is a vibratory PEP therapy device, and that the device is arranged to produce an oscillating resistance to expiration through the device.

8. A method of evaluating use of a respiratory therapy device including a housing having an inlet through which a patient breathes and an outlet through which gas flows, and a movable member mounted between the inlet and the outlet in the housing that is caused to oscillate by the action of breathing through the device so as to provide an oscillating resistance to breathing through the device, characterized in that the method includes the steps of mounting an accelerometer on the housing, and monitoring vibration transmitted through the housing of the device caused by the oscillating movement of the movable member by the accelerometer.

9. The method according to claim 8, characterized in that the method includes the step of storing an indication of periods of sensed vibration.

10. The method according to claim 8, characterized in that the method includes the step of determining vibration frequencies caused by the oscillating movement of the movable member.

11. An apparatus comprising a respiratory therapy device including a housing that includes an inlet through which a patient breathes and an outlet through which gas flows, and a movable member mounted in the housing that is caused to oscillate by the action of breathing through the housing, wherein the use of the apparatus is evaluated by monitoring vibration transmitted through the housing of the device caused by the moveable member by an accelerometer mounted on the housing.

* * * * *